(12) United States Patent
Field et al.

(10) Patent No.: US 8,744,554 B2
(45) Date of Patent: Jun. 3, 2014

(54) REMOVABLE LOCALIZING WIRE

(75) Inventors: Steven E. Field, Grand Rapids, MI (US); Brian R. Mulder, Rockford, MI (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 46 days.

(21) Appl. No.: 13/431,435

(22) Filed: Mar. 27, 2012

(65) Prior Publication Data

US 2012/0239087 A1    Sep. 20, 2012

Related U.S. Application Data

(60) Continuation of application No. 11/534,798, filed on Sep. 25, 2006, now Pat. No. 8,170,648, which is a division of application No. 10/904,666, filed on Nov. 22, 2004, now Pat. No. 8,409,111.

(51) Int. Cl.
*A61B 6/00* (2006.01)

(52) U.S. Cl.
USPC ............... 600/431; 606/1; 606/116; 606/185; 600/562

(58) Field of Classification Search
USPC .............. 606/116, 185, 1; 600/414, 420, 431, 600/434, 562, 564–567
See application file for complete search history.

(56) References Cited

U.S. PATENT DOCUMENTS

| | | | |
|---|---|---|---|
| 2,876,770 A | 3/1959 | White | |
| 2,907,327 A | 10/1959 | White | |
| 3,516,412 A | 6/1970 | Ackerman | |
| 4,007,732 A | 2/1977 | Kvavle et al. | |
| 4,103,690 A | 8/1978 | Harris | |
| 4,405,314 A | 9/1983 | Cope | |
| 4,542,749 A | 9/1985 | Caselgrandi et al. | |
| 4,582,061 A | 4/1986 | Fry | |
| 4,592,356 A | 6/1986 | Gutierrez | |
| 4,616,656 A * | 10/1986 | Nicholson et al. | 600/300 |
| 4,627,420 A | 12/1986 | Katz | |
| 4,634,432 A | 1/1987 | Kocak | |
| 4,669,473 A | 6/1987 | Richards et al. | |
| 4,747,831 A | 5/1988 | Kulli | |
| 4,799,495 A | 1/1989 | Hawkins et al. | |
| 4,874,376 A | 10/1989 | Hawkins, Jr. | |
| 4,909,250 A | 3/1990 | Smith | |
| 4,986,279 A | 1/1991 | O'Neill | |
| 5,057,114 A | 10/1991 | Wittich et al. | |
| 5,059,197 A | 10/1991 | Urie et al. | |
| 5,127,916 A | 7/1992 | Spencer et al. | |

(Continued)

FOREIGN PATENT DOCUMENTS

| | | | |
|---|---|---|---|
| EP | 0385604 A2 | 9/1990 | |
| EP | 0393972 A1 | 10/1990 | |

(Continued)

OTHER PUBLICATIONS

Cook Incorporated: Emoblization and Occlusion. From: www.cookgroup.com 6 ppages, date: 1997.

*Primary Examiner* — Kathleen Holwerda

(57) ABSTRACT

A localizing wire includes an anchor portion that can change shape from a collapsed shape to an expanded shape and thereby anchor within a tissue mass. The localizing wire has an exterior portion that can lie flat against the tissue mass. The localizing wire can be repositioned or withdrawn without the need for the reinsertion of an introducer.

20 Claims, 16 Drawing Sheets

(56) References Cited

U.S. PATENT DOCUMENTS

| | | | |
|---|---|---|---|
| 5,195,540 A | 3/1993 | Shiber | |
| 5,221,269 A | 6/1993 | Miller et al. | |
| 5,273,532 A | 12/1993 | Niezink et al. | |
| 5,282,845 A | 2/1994 | Bush et al. | |
| 5,338,311 A | 8/1994 | Mahurkar | |
| 5,353,804 A | 10/1994 | Kornberg et al. | |
| 5,376,094 A | 12/1994 | Kline | |
| 5,380,290 A | 1/1995 | Makower et al. | |
| 5,417,708 A | 5/1995 | Hall et al. | |
| 5,534,007 A | 7/1996 | St. Germain et al. | |
| 5,542,915 A | 8/1996 | Edwards et al. | |
| 5,697,907 A | 12/1997 | Gaba | |
| 5,749,887 A | 5/1998 | Heske et al. | |
| 5,782,771 A | 7/1998 | Hussman | |
| 5,788,710 A | 8/1998 | Bates et al. | |
| 5,795,339 A | 8/1998 | Erskine | |
| 5,800,445 A | 9/1998 | Ratcliff et al. | |
| 5,879,338 A | 3/1999 | Mahurkar | |
| 5,879,357 A | 3/1999 | Heaton et al. | |
| 5,897,554 A | 4/1999 | Chia et al. | |
| 5,902,310 A | 5/1999 | Foerster et al. | |
| 5,954,655 A | 9/1999 | Hussman | |
| 5,954,670 A | 9/1999 | Baker | |
| 5,976,129 A | 11/1999 | Desai | |
| 5,989,265 A | 11/1999 | Bouquet De La Joliniere et al. | |
| 6,053,925 A * | 4/2000 | Barnhart | 606/116 |
| 6,066,122 A | 5/2000 | Fisher | |
| 6,080,113 A | 6/2000 | Heneveld et al. | |
| 6,090,063 A | 7/2000 | Makower et al. | |
| RE36,885 E | 9/2000 | Blecher et al. | |
| 6,135,993 A | 10/2000 | Hussman | |
| 6,156,013 A | 12/2000 | Mahurkar | |
| 6,161,034 A | 12/2000 | Burbank et al. | |
| 6,175,760 B1 * | 1/2001 | Baskin et al. | 600/436 |
| 6,206,856 B1 | 3/2001 | Mahurkar | |
| 6,228,055 B1 | 5/2001 | Foerster et al. | |
| 6,241,665 B1 | 6/2001 | Negus et al. | |
| 6,261,302 B1 | 7/2001 | Voegele et al. | |
| 6,267,732 B1 | 7/2001 | Heneveld et al. | |
| 6,312,429 B1 | 11/2001 | Burbank et al. | |
| 6,336,904 B1 | 1/2002 | Nikolchev | |
| 6,340,367 B1 | 1/2002 | Stinson et al. | |
| 6,364,895 B1 | 4/2002 | Greenhalgh | |
| 6,371,904 B1 | 4/2002 | Sirimanne et al. | |
| 6,383,145 B1 | 5/2002 | Worm et al. | |
| 6,405,733 B1 | 6/2002 | Fogarty et al. | |
| 6,409,742 B1 | 6/2002 | Fulton, III et al. | |
| 6,427,081 B1 | 7/2002 | Burbank et al. | |
| 6,482,178 B1 | 11/2002 | Andrews et al. | |
| 6,540,693 B2 | 4/2003 | Burbank et al. | |
| 6,544,269 B2 | 4/2003 | Osborne et al. | |
| 6,547,762 B1 | 4/2003 | Botich et al. | |
| 6,551,253 B2 | 4/2003 | Worm et al. | |
| 6,564,806 B1 | 5/2003 | Fogarty et al. | |
| 6,567,689 B2 | 5/2003 | Burbank et al. | |
| 6,575,991 B1 | 6/2003 | Chesbrough et al. | |
| 6,582,402 B1 | 6/2003 | Erskine | |
| 6,638,234 B2 | 10/2003 | Burbank et al. | |
| 6,679,851 B2 * | 1/2004 | Burbank et al. | 600/564 |
| 6,685,666 B1 | 2/2004 | Fontenot | |
| 6,716,179 B2 | 4/2004 | Burbank et al. | |
| 6,752,154 B2 | 6/2004 | Fogarty et al. | |
| 6,766,186 B1 | 7/2004 | Hoyns et al. | |
| 6,813,520 B2 | 11/2004 | Truckai et al. | |
| 6,824,527 B2 | 11/2004 | Gollobin | |
| 6,936,014 B2 | 8/2005 | Vetter et al. | |
| 6,951,564 B2 | 10/2005 | Espositio et al. | |
| 7,001,341 B2 | 2/2006 | Gellman et al. | |
| 7,044,957 B2 | 5/2006 | Foerster et al. | |
| 7,125,397 B2 | 10/2006 | Woehr et al. | |
| 7,424,320 B2 | 9/2008 | Chesbrough et al. | |
| 7,520,881 B2 | 4/2009 | Foushee et al. | |
| 8,131,346 B2 | 3/2012 | Chesbrough et al. | |
| 8,170,648 B2 * | 5/2012 | Field et al. | 600/431 |
| 2001/0003791 A1 | 6/2001 | Burbank et al. | |
| 2001/0023322 A1 | 9/2001 | Espositio et al. | |
| 2001/0034528 A1 | 10/2001 | Foerster et al. | |
| 2002/0019595 A1 | 2/2002 | Osborne et al. | |
| 2002/0035324 A1 | 3/2002 | Sirimanne et al. | |
| 2002/0052564 A1 | 5/2002 | Burbank et al. | |
| 2002/0077687 A1 | 6/2002 | Ahn | |
| 2002/0143359 A1 | 10/2002 | Fulton, III et al. | |
| 2002/0193815 A1 | 12/2002 | Foerster et al. | |
| 2003/0028236 A1 | 2/2003 | Gillick et al. | |
| 2003/0225420 A1 | 12/2003 | Wardle | |
| 2004/0049224 A1 | 3/2004 | Buehlmann et al. | |
| 2004/0073107 A1 | 4/2004 | Sioshansi et al. | |
| 2004/0106891 A1 | 6/2004 | Langan et al. | |
| 2004/0116805 A1 * | 6/2004 | Chesbrough et al. | 600/431 |
| 2004/0122312 A1 | 6/2004 | Chesbrough et al. | |
| 2004/0127765 A1 | 7/2004 | Seiler et al. | |
| 2004/0162574 A1 | 8/2004 | Viola | |
| 2005/0075606 A1 | 4/2005 | Botich et al. | |
| 2006/0074443 A1 | 4/2006 | Foerster et al. | |
| 2006/0111629 A1 | 5/2006 | Field et al. | |
| 2007/0021764 A1 | 1/2007 | Field et al. | |
| 2008/0033280 A1 | 2/2008 | Lubock et al. | |
| 2008/0097199 A1 | 4/2008 | Mullen | |

FOREIGN PATENT DOCUMENTS

| | | |
|---|---|---|
| EP | 0395997 A1 | 11/1990 |
| EP | 0415504 A1 | 3/1991 |
| EP | 0481685 A1 | 4/1992 |
| EP | 0769280 A2 | 4/1997 |
| EP | 0769281 A2 | 4/1997 |
| EP | 0937443 A2 | 8/1999 |
| EP | 1163888 A1 | 12/2001 |
| EP | 1306097 A1 | 5/2003 |
| EP | 1317938 A1 | 6/2003 |
| FR | 2776165 A1 | 9/1999 |
| GB | 786850 | 11/1957 |
| WO | 9632892 A1 | 10/1996 |
| WO | 9908607 A1 | 2/1999 |
| WO | 0024320 A1 | 5/2000 |
| WO | 0024332 A1 | 5/2000 |
| WO | 2004045444 A2 | 6/2004 |

* cited by examiner

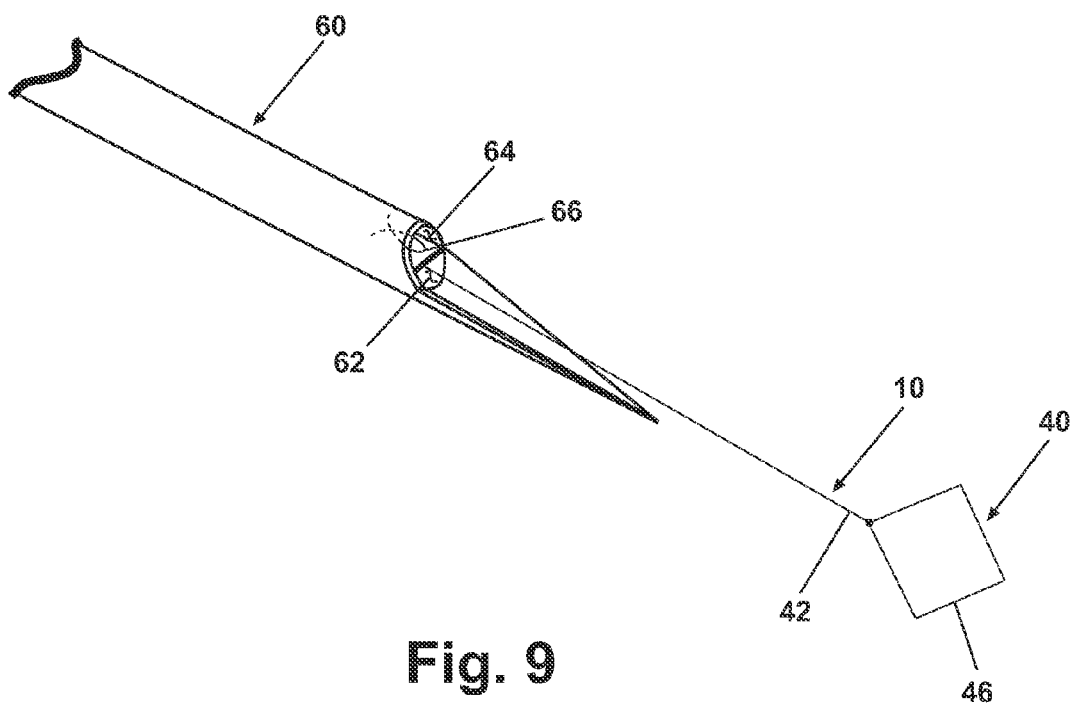

REMOVABLE LOCALIZING WIRE

CROSS REFERENCE TO RELATED APPLICATION

This application is a continuation of U.S. patent application Ser. No. 11/534,798, filed Sep. 25, 2006, now U.S. Pat. No. 8,170,648, which is a divisional of U.S. patent application Ser. No. 10/904,666, filed Nov. 22, 2004, now U.S. Pat. No. 8,409,111.

BACKGROUND OF THE INVENTION

1. Field of the Invention

The invention relates generally to localizing wires and more particularly to a localizing wire which comprises an anchor portion having collapsible properties enabling the anchor portion to be retracted into a cannula lumen for repositioning or removal in a tissue mass. In another aspect, the invention relates to a localizing wire configured such that an externally extending portion of the wire can lie against the exterior of the tissue mass. In yet another aspect, the invention relates to a method of using the localizing wire. In one other aspect, the invention relates to a localizing wire that can be removed from a tissue mass without the re-introduction of a cannula.

2. Description of the Related Art

Localizing wires are well-known devices for marking areas, such as lesions, in a tissue mass, frequently breast tissue. When such a lesion is identified with a medical imaging technique, such as radiography or ultrasonography, it is often desirable to position a localizing wire or other type of imaging marker near the lesion to facilitate locating the lesion during later procedures, such as biopsy or surgery. Alternatively, a localizing wire, tissue marker or staple can be placed in the tissue mass after a biopsy has been performed. In the latter case, the localizing wire marks the location of the biopsy cavity for future procedures.

Localizing wires typically comprise an anchor portion implanted at the tissue site of interest, with a wire portion extending from the anchor portion to exit through the skin. A practitioner can then use the wire as a visual and tactile guide to the lesion rather than solely relying on imaging techniques, which currently provide good 2-D images but not 3-D images. During surgery, surgeons typically prefer a localizing wire to locate the lesion because it leads them straight to the biopsy site.

To implant a localizing wire, a needle, or cannula, is inserted into the tissue mass and, with guidance from an imaging system, is positioned with its tip at a selected location at or near the lesion. Once the needle is in place, the localizing wire is extended through the needle and out the tip into or adjacent the lesion where the hook on the end of the wire engages the tissue mass. Thereafter, the needle is removed from the tissue mass, and the localizing wire remains anchored in place by the hook.

It is critical that the localizing wire be accurately placed at the desired location within the tissue and remain in the desired location. Movement of the localizing wire after it is properly located and implanted is very undesirable as it will not properly identify the lesion or the biopsy site if a follow-up surgery is required.

However, there is often a need to reposition the localizing wire after the initial implantation. For a variety of reasons, such as, for example, the nature of the instrument used for implanting, the initial implantation may not always be located at the desired site. Under such circumstances, the localizing wire will need to be repositioned. Thus, a contemporary localizing wire must perform the conflicting functions of keeping the localizing wire anchored at the desired implantation site while permitting the repositioning of the localizing wire.

Prior localizing wires accomplished these conflicting functions by the anchor having a pointed, hook shape and being formed of a memory metal, such as Nitinol. When the localizing wire was stored in the cannula, the anchor was substantially straight and took on the hook shape only as it was extended exteriorly of the cannula. As the anchor was extended from the cannula, it pierced the surrounding tissue and formed the hook shape to anchor the localizing wire to the tissue. The localizing wire could be repositioned by withdrawing the anchor back into the cannula to straighten out the hook. The cannula would then be repositioned and the anchor once again extended to anchor the wire. The curvature of the hook shape was great enough that the anchor would not defect in response to an external pulling on the wire.

While the prior localizing wire adequately accomplished the conflicting functions, it does have certain known disadvantages. One such disadvantage is that the tissue is pierced each time the localizing wire is repositioned, which causes additional trauma. It is better to minimize the trauma to the surrounding tissue for reduced recovery time and the patient's comfort. Thus, there remains a need for a device that can reimplant or remove a localizing wire in a tissue mass after initial implantation with minimal discomfort to a patient.

Another disadvantage of current localizing wires is that, after implantation, a portion of the localizing wire extends exteriorly of the tissue. This exteriorly extending portion of the localizing wire projects away from the surface of the tissue mass. While the projecting of the exterior portion of the wire is useful for the surgeon in locating the localizing wire during surgery, it creates the risk that the patient or someone else might accidentally catch the exteriorly extending portion and pull or tug on the localizing wire, resulting in the possible repositioning of the localizing wire inside the tissue. Such an accidental repositioning is very undesirable in that the localizing wire will no longer properly locate the lesion and it can be painful for the patient. This is one of the reasons why localizing wires are typically inserted just prior to the surgery and are not intended to be left in the tissue mass for an extended period.

In practice, because of the several hour or several day delay between the time that a biopsy is taken and the results of the tissue analysis is received, it is a common practice for an internal imaging marker, such as that disclosed in U.S. Pat. No. 6,575,991, to be placed at the biopsy site. If the analysis of the tissue indicates that follow-up surgery is required, then a localizing wire is placed within the tissue at the site of the internal imaging marker prior to surgery and the surgeon uses the localizing wire to locate the biopsy site. It is desirable to have a localizing wire that can be used instead of the internal imaging marker to mark the biopsy site, left within the tissue for an extended period of time, and used to guide the surgeon if surgery is required or easily removed if surgery is not required.

SUMMARY OF THE INVENTION

The invention relates to a method of marking a lesion in a tissue mass with a localizing wire. The method comprises installing a localizing wire into a cannula having at least one lumen. The localizing wire comprising a localizing thread and a localizing anchor having a collapsed shape delineating a first area in the at least one lumen and an expanded shape delineating a second area greater than the first area outside the at least one lumen. The cannula is inserted into the tissue mass. One of the localizing wire and the cannula is moved to place the localizing anchor outside the at least one lumen at a first selected location relative to the lesion so that the localizing anchor expands from the first to the second shape to exert an expansive force against the tissue mass.

The method can further comprise retracting the localizing anchor into the at least one lumen to return the localizing anchor from the expanded shape to the collapsed shape. The cannula can then be repositioned to relocate the localizing member at a second selected location relative to the lesion. The cannula can be withdrawn from the tissue mass with the localizing anchor remaining in the selected location and the localizing thread extending exterior of the tissue.

The method can further comprise reinserting the cannula into the tissue mass with the localizing thread extending through the at least one lumen followed by retracting the localizing anchor into the at least one lumen to return the localizing anchor from the expanded shape to the collapsed shape, and then withdrawing the cannula with the localizing wire therein to remove the localizing wire from the tissue mass.

The cannula can comprise multiple lumens, with an imaging marker installed into one of the lumens. The imaging marker or the cannula can then be moved to place the imaging marker at a selected location relative to the lesion.

The invention also relates to a localizing wire for marking the location of a lesion in a tissue mass. The localizing wire is adapted for placement through at least one cannula lumen relative to the lesion. The localizing wire comprises a localizing anchor for holding the localizing wire at a selected location within the tissue mass relative to the lesion. A localizing thread connects to the localizing anchor and is sized to extend outside the tissue mass when the localizing anchor is held at the selected location. The localizing anchor has a collapsed shape delineating a first area when the localizing anchor is in the at least one lumen and an expanded shape delineating a second area larger than the first area when the localizing anchor is outside the at least one lumen.

The localizing thread can be made of wire. The anchor can have many different shapes when expanded. Some of the expanded shapes include a square, triangle, and circle. The anchor can also be disk shaped.

The localizing anchor and the localizing thread can be made of the same piece or can be separate pieces connected together.

The localizing anchor can be withdrawn into the at least one lumen after the localizing anchor has been placed at the selected location relative to the lesion by changing the anchor from the expanded shape to the collapsed shape. The shape of the localizing anchor can be changed from the expanded shape to the collapsed shape by pulling on the localizing thread, whether the localizing wire is extending through the cannula or not.

The at least one lumen comprises multiple lumens. An imaging marker can be installed in one of the multiple lumens.

The localizing anchor is made from resilient material and inherently expands from the collapsed shape to the expanded shape to exert a force against the tissue mass, with the localizing anchor displacing but not puncturing the tissue mass when the localizing anchor expands from the collapsed to the expanded shape.

The invention relates to a method of marking a lesion in a tissue mass with a localizing wire. The method comprises installing a localizing wire into a cannula having at least one lumen. The localizing wire comprising a localizing thread and a localizing anchor having a collapsed shape delineating a first area in the at least one lumen and an expanded shape delineating a second area greater than the first area outside the at least one lumen. The cannula is inserted into the tissue mass. One of the localizing wire and the cannula is moved to place the localizing anchor outside the at least one lumen at a first selected location relative to the lesion so that the localizing anchor exerts an expansive force against the tissue mass at the selected location relative to the lesion when the localizing anchor transitions from the collapsed shape to the expanded shape.

The invention also relates to a localizing wire for insertion in a tissue mass, comprising an anchor for at least temporarily fixing the localizing wire in the tissue mass, and a thread coupled to the anchor and being configured such that an exterior portion of the thread extending exteriorly of the tissue mass can lie substantially flat against the exterior of the tissue mass.

The thread can be configured to lie substantially flat against the exterior of the tissue mass by: the thread bending without plastic deformation; the thread bending under its own weight; and/or selecting the cross-sectional area and/or the Young's Modulus of the thread. The thread can lie substantially flat against the tissue mass such that there is no gap between the tissue mass and the external portion of the thread near the insertion point into the tissue mass. While all of the external portion can lie flat against the tissue mass, at least a portion of the localizing wire near the insertion point is configured to lie substantially flat against the exterior of the tissue mass.

At least the portion of the thread near the insertion point can be made from annealed steel to provide the desired Young's Modulus.

The invention further relates to a method of positioning a localizing wire in a tissue mass, with the localizing wire comprising a thread and an anchor coupled to the thread. The method comprises inserting the localizing wire into the tissue mass such that the anchor is received within the tissue mass and a portion of the thread extends beyond the exterior of the tissue mass, and laying the external portion of the thread such that it is substantially flat against the exterior of the tissue mass.

The laying step can be accomplished by bending the external portion of the thread without any plastic deformation of the thread. The bending of the external portion can be effected by the weight of the external portion. The laying can be such that there is substantially no gap between the exterior of the tissue mass and the portion of the external portion near the insertion point of the localizing wire into the tissue mass. Also, the entire external portion can lie substantially flat against the exterior of the tissue mass.

The method can further comprise fixing the external portion to the exterior of the tissue mass. The fixing can be accomplished by taping the external portion to the exterior of the tissue mass.

In another aspect, the invention relates to a localizing wire for locating a site within a tissue mass and implantable within the tissue mass using an introducer. The localizing wire comprising a thread to which is mounted an anchor and an actuator. The anchor has an alterable configuration that is alterable between an anchor configuration and a release configuration. The actuator is mounted to the localizing wire for relative movement therewith between an anchor position, where the anchor assumes the anchor configuration, and a removal position, where the anchor assumes the release configuration. The actuator is accessible exteriorly of the tissue mass after the localizing wire is implanted to permit the release of the anchor and the withdrawal of the localizing wire without a subsequent surgical procedure.

The actuator can comprise a shroud that is slidably mounted to the localizing wire, with the shroud at least partially covering the hook when the actuator is in the removal position. The shroud can be of a length such that a portion of the shroud extends beyond the exterior of the tissue mass after the localizing wire is implanted.

The shroud can further comprise an elongated sheath defining a hollow interior in which the thread is slidably received. The sheath can be flexible. The sheath can have proximal and distal ends, wherein when the localizing wire is moved to the release position, the proximal end bears against the anchor to move the anchor to the release configuration. When the localizing wire is implanted the distal end extends beyond the exterior of the tissue mass.

The thread and sheath are configured such that the sheath can be slidably removed from the thread. The sheath can be of many forms and is especially a tube or a coil spring. The tube can made of plastic, which can be transparent.

The combination of the sheath and the thread can be configured such that a portion of the combined thread and sheath extends exteriorly of the tissue mass and can lie substantially flat against the exterior of the tissue mass. The portion of the combined thread and sheath can have a bending portion that bends without plastic deformation so that the portion of the combined thread and sheath can lie substantially flat against the exterior of the tissue mass. The bending portion can be configured to bend under its own weight. The portion of the combined thread and sheath can be configured to lie substantially flat against the tissue mass by selecting at least one of the cross sectional area and the Young's Modulus of the combined portion of the thread and sheath. The combined thread and sheath can be configured to lie substantially flat against the tissue mass such that there is no gap between the tissue mass and the portion of the combined thread and sheath near the insertion point into the tissue mass.

The invention further relates to a method of implanting and removing, into a tissue mass, a localizing wire having a reconfigurable anchor. The method comprises: inserting the localizing wire into the tissue mass; configuring the anchor into an anchoring configuration where the anchor anchors the localizing wire in the tissue mass; reconfiguring the anchor from the anchoring configuration to a release configuration, where the anchor does not anchor the localizing wire in the tissue mass; and withdrawing the localizing wire with the anchor in the release configuration from the tissue mass.

The insertion of the localizing wire can comprise inserting an introducer with a hollow interior into the tissue mass and inserting the localizing wire into the hollow interior of the introducer. The introducer can then be drawn away from the anchor after the inserting of the localizing wire in the tissue mass to expose the anchor. The withdrawing of the introducer comprises completely removing the introducer from the tissue mass. The withdrawing of the introducer effects the reconfiguring of the anchor from the anchoring configuration to a release configuration.

The inserting of the localizing wire into the introducer can occur prior to or after the inserting of the introducer into the tissue mass. The configuring of the anchor into the anchoring configuration can be effected by relatively moving the introducer and the localizing wire. The relative movement of the introducer and the localizing wire comprises moving the localizing wire relative to the introducer.

The configuring of the anchor into the anchor position need not occur after the insertion of the localizing wire. The anchor can be in the anchoring configuration prior to the insertion of the localizing wire.

The method can further comprise sliding a sheath on the localizing wire to configure the anchor. The sheath can be slid toward the anchor to place the anchor in the release configuration. Additionally, the sheath can be slid away from the anchor to place the anchor in the anchoring configuration. The anchor can be at least partially received within the sheath when the anchor is in the release configuration.

The method can also comprise laying a portion of the localizing wire extending beyond the exterior of the tissue mass against the exterior of the tissue mass. The exterior portion of the localizing wire can be secured to the exterior of the tissue mass. The securing can be effected by taping the exterior portion of the localizing wire to the exterior of the tissue mass.

The withdrawing of the introducer can comprise completely removing the introducer from the tissue mass. The withdrawing of the introducer also can effect the reconfiguring the anchor from the anchoring configuration to a release configuration.

BRIEF DESCRIPTION OF THE DRAWINGS

In the drawings:

FIG. 9 is an enlarged perspective view of an alternate embodiment of a cannula having a first lumen for receiving the localizing wire and a second lumen.

DESCRIPTION OF AN EMBODIMENT OF THE INVENTION

Figure 1:
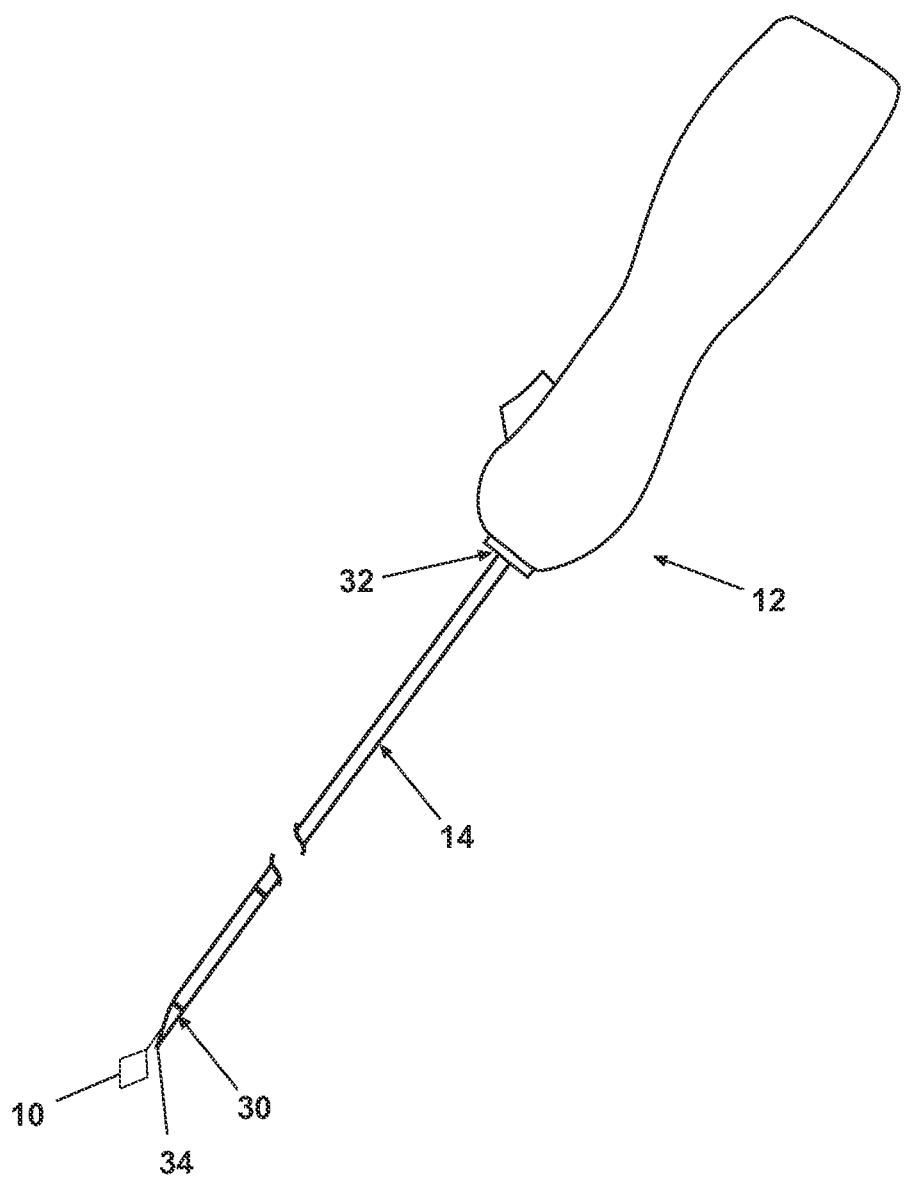
FIG. 1 is a side view of a localizing wire introducer having a cannula containing a first embodiment of a localizing wire comprising a thread and an anchor, with the anchor extending from the cannula and in an expanded condition.
Figure 2:
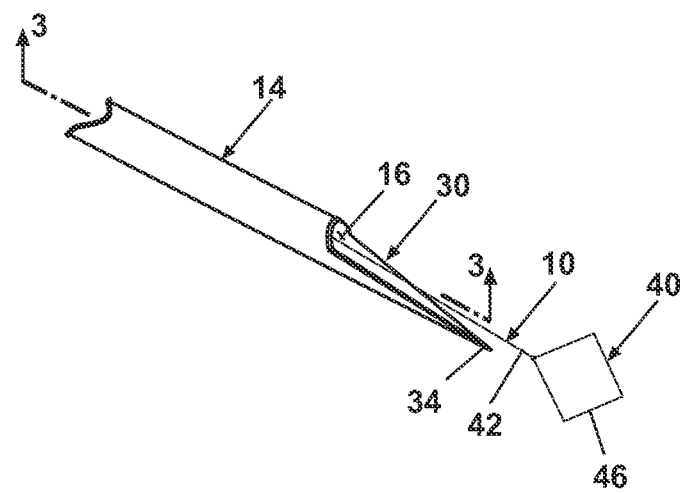
FIG. 2 is a close-up perspective view of the end of the cannula illustrated in FIG. 1.

Referring now to the figures, and particularly to FIG. 1, an embodiment of the invention is illustrated comprising a localizing wire 10 operably communicating with a well-known introducer 12 having a cannula 14. The cannula 14 comprises a distal end 30 having an insertion tip 34 and a proximal end 32. As best seen in FIG. 2, the cannula 14 defines a lumen 16 through which the localizing wire 10 is placed.

Referring to FIGS. 1-4, the localizing wire 10 comprises a localizing anchor 40 and a localizing thread 42. When mounted in the introducer 12 prior to implantation (FIG. 3), the anchor 40 is contained within the lumen 16 and a portion of the localizing thread extends exteriorly from the rear of the introducer (FIG. 1). However, it is not necessary for the thread to extend exteriorly of the introducer. The thread can be contained within the interior of the introducer.

Figure 3:
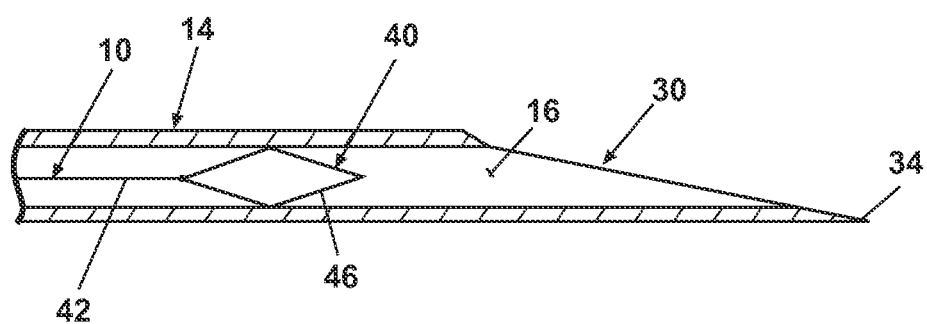
FIG. 3 is a sectional view taken along view line 3-3 of FIG. 2 illustrating the anchor received within the cannula and in a collapsed condition.
Figure 4:
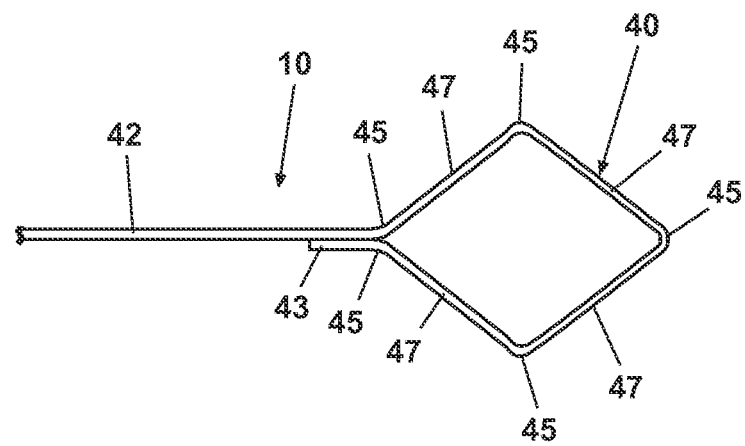
FIG. 4 is an enlarged side view of the localizing thread and localizing anchor illustrated in FIG. 2 in the expanded condition.

The localizing anchor 40 is fabricated of a resilient, physiologically inert material such as stainless steel or titanium wire, which can assume a first collapsed configuration in the lumen 16 as illustrated in FIG. 3, and a second expanded configuration outside the lumen 16 as illustrated in FIGS. 1, 2 and 4.

Referring to FIG. 4, the anchor 40 of the localizing wire 10 is shown in greater detail. As illustrated, the anchor 40 is formed from the same wire as the thread 42. In other words, the anchor 40 is a continuation of the localizing thread 42, with an end 43 of the anchor 40 being connected to the thread 42 to complete the anchor 40. The end 43 can be bonded or welded to the thread 42 to form the connection.

The anchor 40 has a diamond or square shape when it is in the expanded condition as illustrated in FIG. 4. The diamond shape is formed by providing multiple bends 45 along the portion of the wire forming the anchor 40, which define therebetween corresponding segments 47. The bends 45 function as hinges about which the segments can move to permit the anchor to transition between the collapsed (FIG. 3) and expanded (FIG. 4) conditions.

Figure 5:
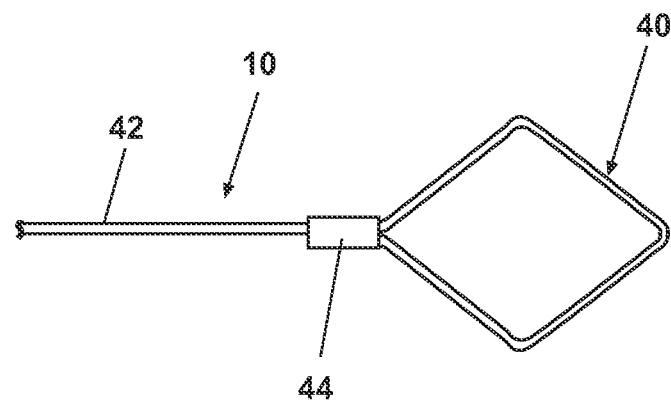
FIG. 5 is an enlarged side view of a second embodiment of the localizing thread and localizing anchor illustrated in FIG. 4.

While the anchor 40 is shown as a continuation of the thread 42 in FIG. 4, FIG. 5 illustrates an alternative where the localizing anchor 40 and the localizing thread 42 comprise separate elements, with the localizing anchor 40 attached to the localizing thread 42 through a suitable connector 44, such as a crimped or interference-fit collar, a weld, or the like. With a separate localizing anchor 40 and localizing thread 42, different materials can be used for each element. For example, the localizing anchor 40 could be formed of a material having a resiliency that would be suitable for the shape-changing properties described herein, but unsuitable for the localizing thread 42. Conversely, the localizing thread 42 could comprise a material having a stiffness that would be unsuitable for the localizing anchor 40.

Figure 6:
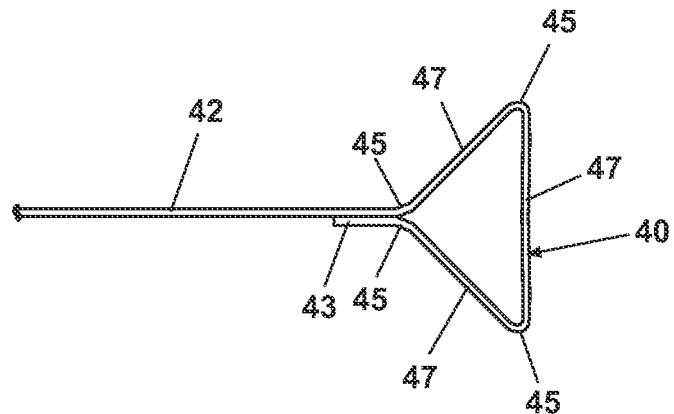
FIG. 6 is an enlarged side view of a third embodiment of the localizing thread and localizing anchor, with the anchor shown in the expanded condition.
Figure 6A:
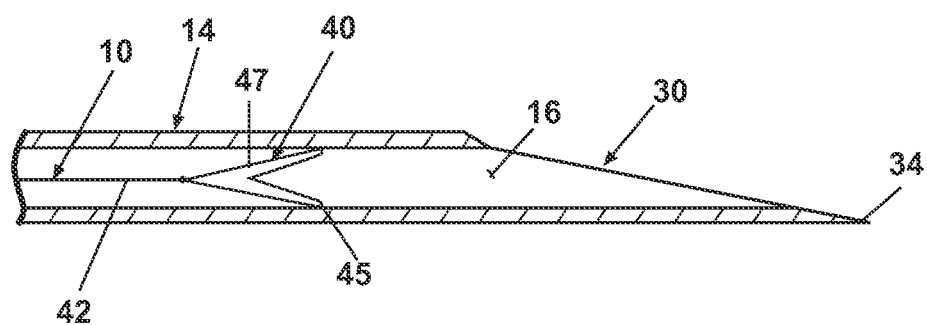
FIG. 6A is an enlarged view of the third embodiment shown in a collapsed condition within the cannula.
Figure 7:
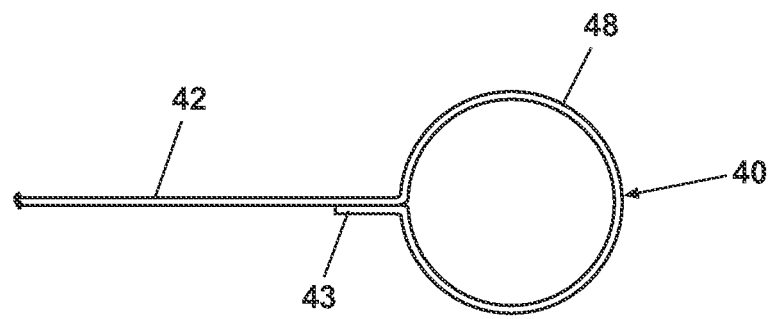
FIG. 7 is an enlarged side view of a fourth embodiment of the localizing thread and localizing anchor.
Figure 7A:
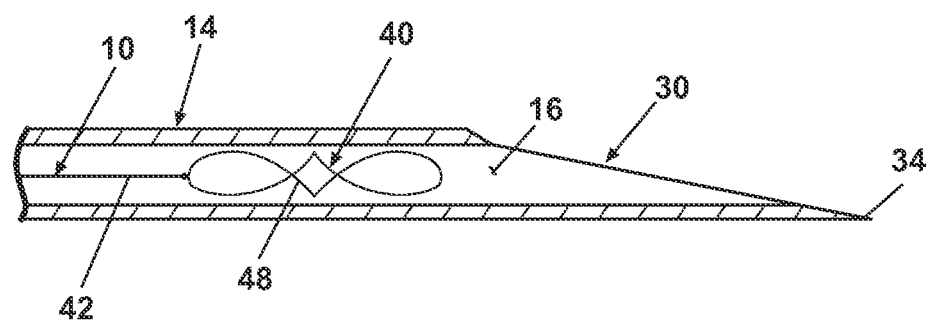
FIG. 7A is an enlarged view of the fourth embodiment shown in a collapsed condition within the cannula.

The localizing anchor 40 can be formed with different shapes which can be selected based upon, for example, the density of the tissue into which the localizing anchor 40 is to be placed, the size of the lesion of interest, the anchoring force required, and the like. In addition to the diamond shape of FIG. 4, the localizing anchor 40 can have a generally triangular shape in the expanded condition as shown in FIG. 6. The triangular shape is shown in the collapsed condition in FIG. 6A. FIGS. 7 and 7A illustrate another shape for the localizing anchor 40, which has the shape of a ring 48 in the expanded condition.

The anchor shapes illustrated in FIGS. 3-7A are similar in that they are of a thread type structure that encloses an area. When the anchor 40 is in the expanded condition, the enclosed area is much greater than when in the collapsed condition. These shapes have no sharp edges that would penetrate the surrounding tissue, yet they still anchor the localizing wire. The lack of penetrating edges reduces the trauma to the patient during repositioning.

Figure 8:
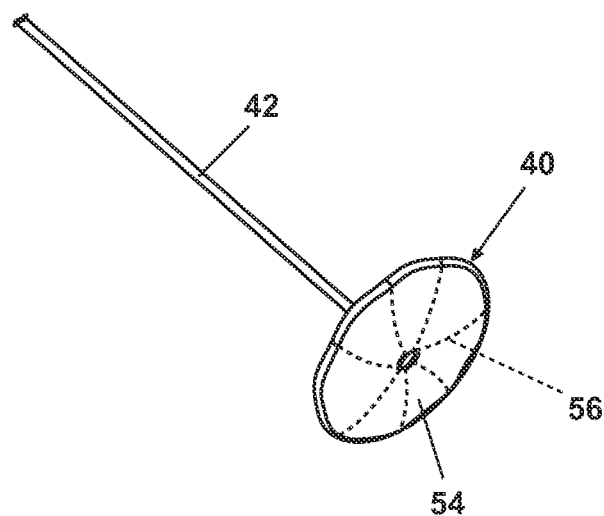
FIG. 8 is an enlarged perspective view of a sixth embodiment of the localizing thread and localizing anchor.
Figure 8A:
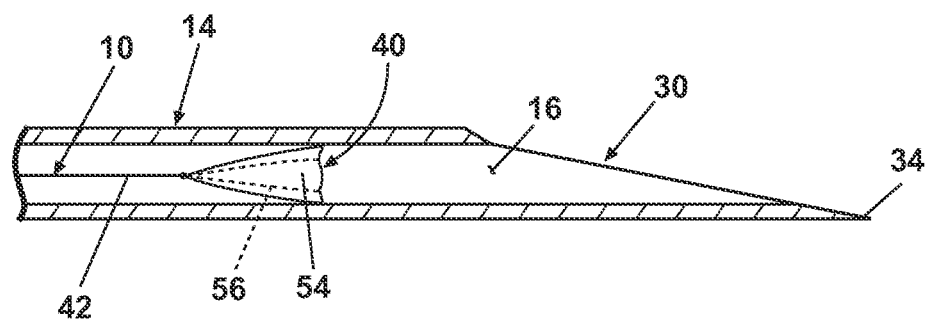
FIG. 8A is an enlarged view of the sixth embodiment shown in a collapsed condition within the cannula.

FIGS. 8 and 8A illustrate another localizing anchor 40 comprising a disc 54, preferably formed with regularly-spaced fold lines 56 for collapsing the disc 54, similar to an umbrella.

As illustrated in FIG. 9, a dual-lumen cannula 60 can be utilized comprising a primary lumen 62 and a secondary lumen 64. The primary lumen 62 carries the localizing wire 10, while the secondary lumen 64 can carry a conventional imaging marker 66 such as that disclosed in U.S. Pat. No. 6,575,991, which is incorporated by reference, or can be used for the introduction of dye, irrigating fluid, pharmaceuticals, and the like, such as that disclosed in co-pending U.S. patent application Ser. No. 10/604,948, filed Aug. 28, 2003.

Figure 10A:
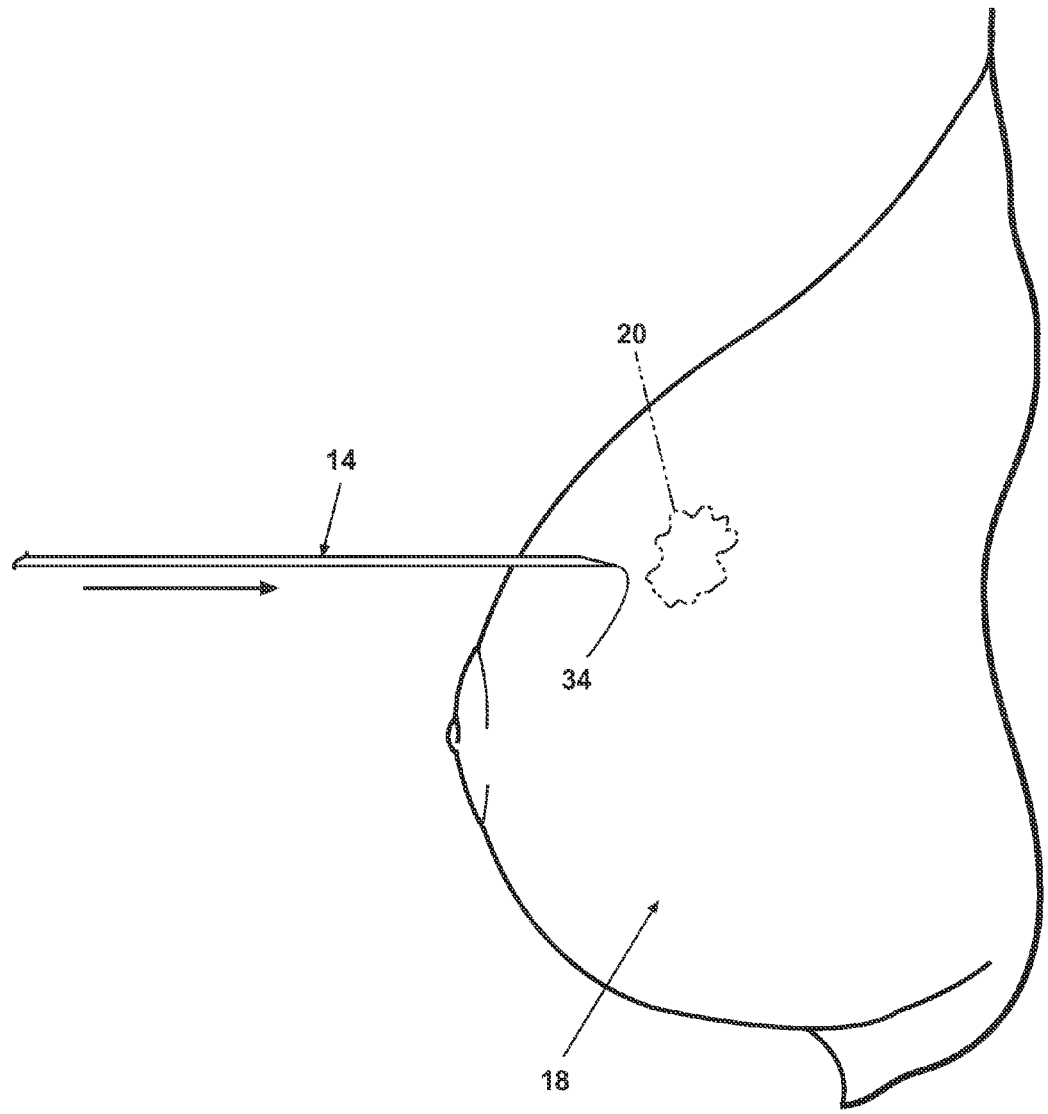
FIGS. 10A-E are side elevation views illustrating a process of placing the localizing wire at a selected location in a tissue of interest.
Figure 10B:
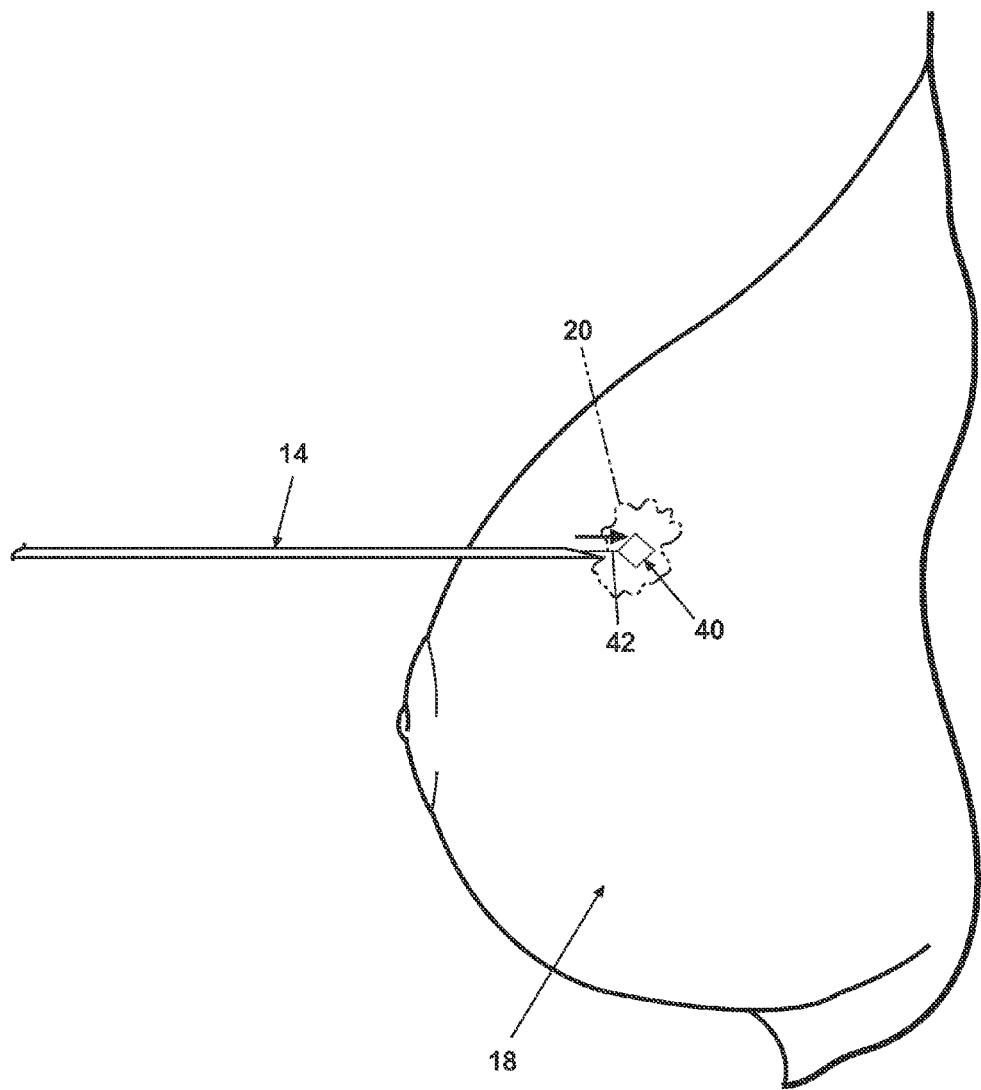

Referring now to FIGS. 10A-E, the localizing wire 10 is utilized as follows. The localizing wire 10 is first loaded into the lumen 16 for introduction of the cannula 14 into the tissue of interest 18. As illustrated in FIG. 10A, the cannula 14 is introduced into the tissue 18 so that the insertion tip 34 is at the location of interest 20, for example adjacent to or penetrating the lesion. As shown in FIG. 10B, the localizing wire 10 is then placed at the location of interest 20 by relatively moving the localizing wire 10 and the cannula 14 to expose the anchor 40 beyond the cannula 14. The relative movement is traditionally accomplished by advancing the localizing wire 10 relative to the cannula 14. However, the cannula can be retracted relative to the localizing wire 10 as disclosed in U.S. patent application Ser. No. 10/707,043, filed Nov. 17, 2003, entitled Apparatus And Method For Implanting A Preloaded Localization Wire, whose disclosure is incorporated by reference.

Figure 10C:
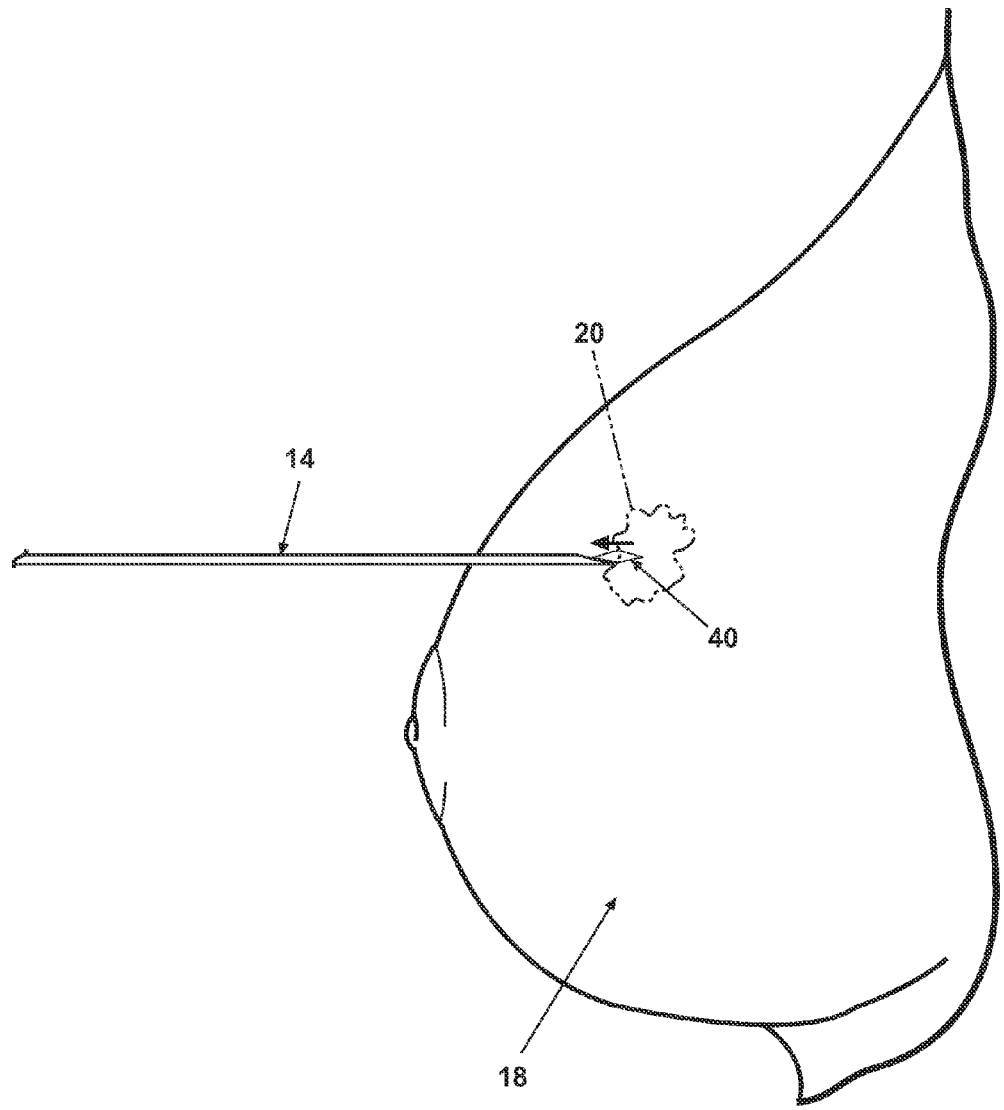

As the localizing anchor 40 exits the end of the cannula, it expands from the collapsed to the expanded condition. As it expands into the surrounding tissue, the anchor 40 compresses and/or displaces the adjacent tissue sufficiently to imbed the localizing anchor 40 in the tissue at the location of interest, but does not puncture the tissue as with a hook-type anchor. If the localizing anchor 40 is not satisfactorily placed at the selected location, the localizing wire 10 can be retracted into the lumen 16 as shown in FIG. 10C by pulling on the localizing thread 42 and drawing the anchor 40 back into the cannula. As the anchor 40 contacts the cannula 12, the interference between the cannula 12 and the anchor collapses the anchor 40 from the expanded to the collapsed condition.

Figure 10D:
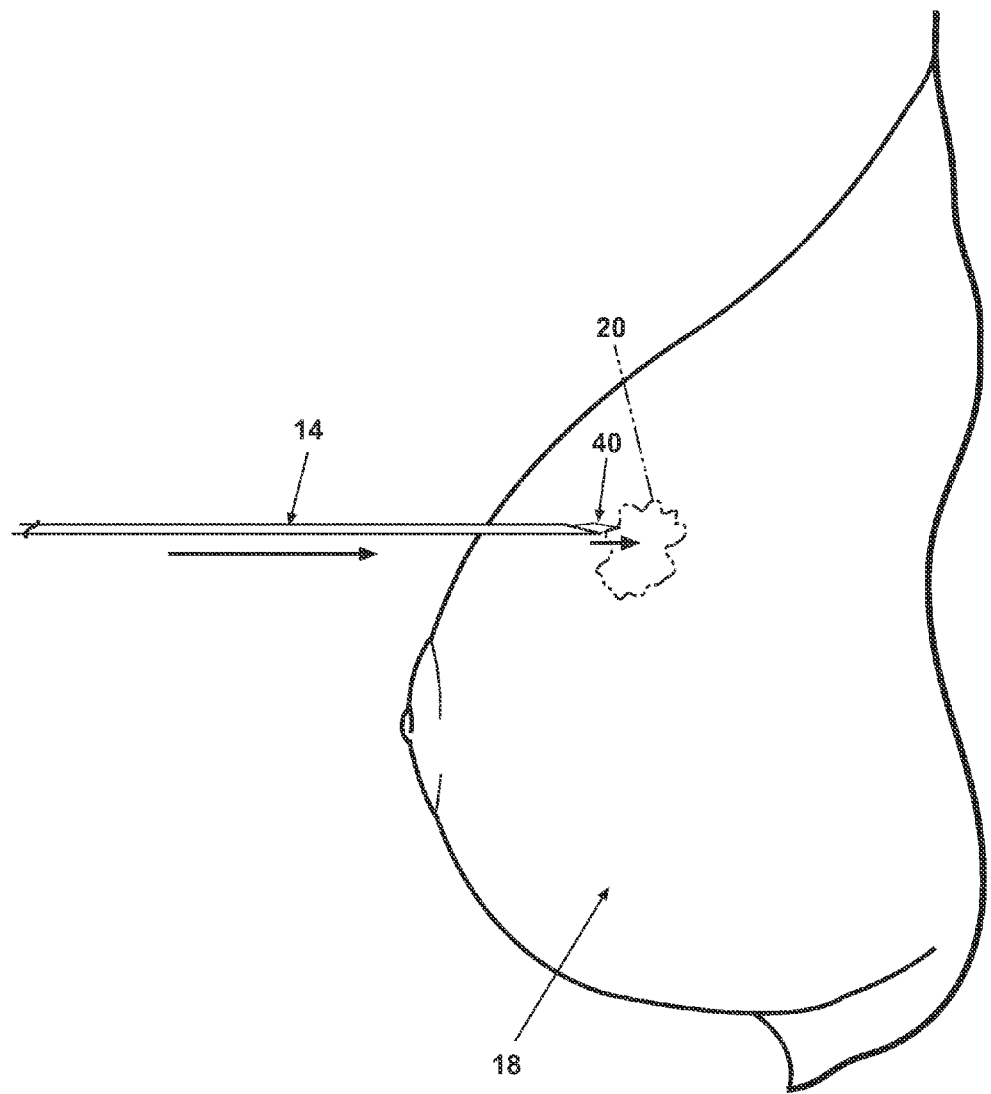
Figure 10E:
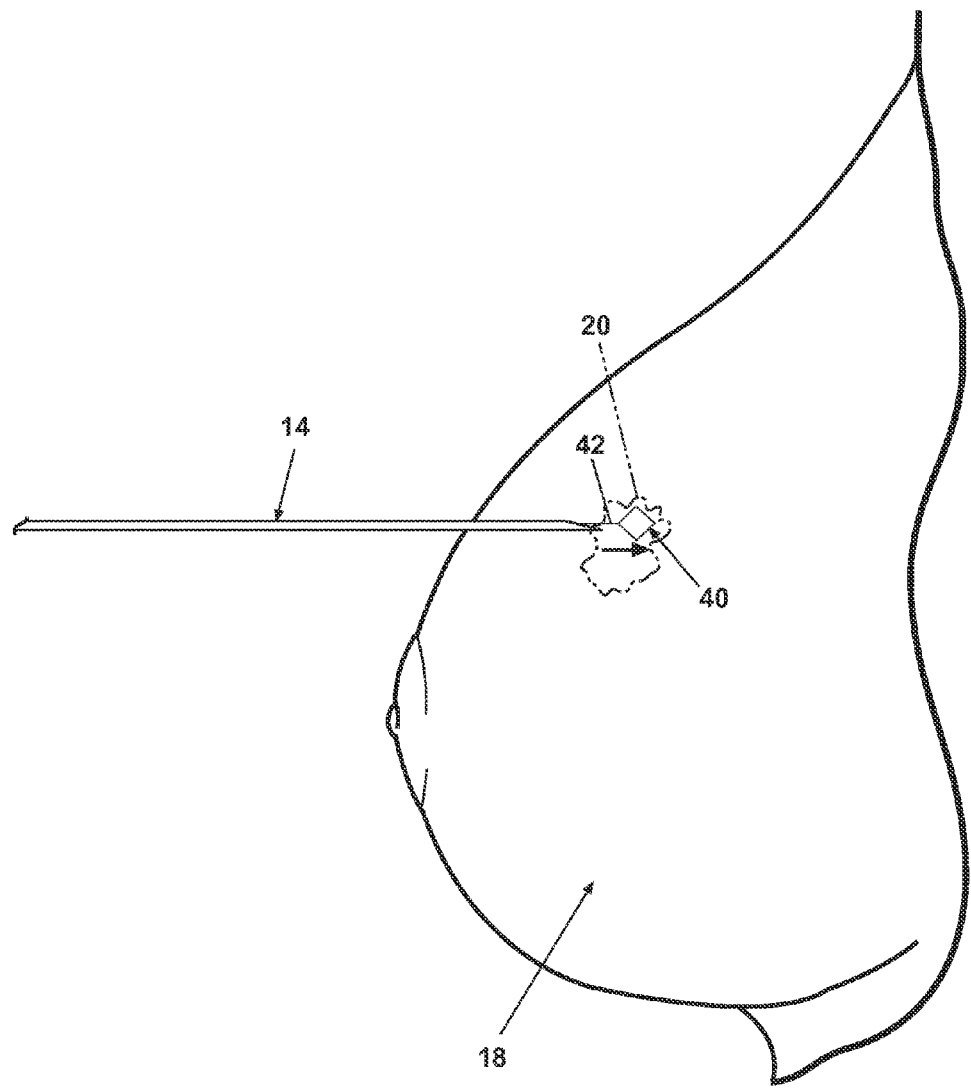

As shown in FIGS. 10D-E, the cannula 14 can then be repositioned and the localizing wire 10 ejected from the lumen 16 into the new location. The cannula 14 can then be removed from the tissue 18, leaving the localizing wire 10 in place with the localizing anchor 40 at the location of interest, and the localizing thread 42 extending outside the tissue 18 as with a conventional localizing wire.

Removal of the localizing wire 10 can be accomplished by passing the cannula 14 over the localizing thread 42 and inserting the cannula 14 into the tissue 18 to the localizing anchor 40. The localizing anchor 40 can then be retracted into the lumen 16, followed by removal of the cannula 14 from the tissue 18. Alternatively, the localizing anchor 40 can be repositioned as discussed above. The localizing wire 10 can also be removed without the reintroduction of the cannula 14 by merely pulling the localizing thread 42 away from the tissue 18. The localizing anchor 40 will be urged into a collapsed configuration by the tissue 18 to facilitate removal of the localizing anchor 40 from the tissue 18.

Prior localizing wires using a hook-shaped anchor that pierced the tissue could not be removed from the tissue without causing substantial tissue trauma unless a cannula was used. The localizing wire 12 can be removed without a cannula with a sufficient force, but will not cause the same trauma to the surrounding tissue as the prior art devices since the anchor 40 does not rely on piercing the tissue for anchoring.

The localizing wire described herein has the advantage of being readily repositionable through retraction of the localizing wire into the lumen of a cannula after the localizing wire has been expelled from the lumen. Unlike prior art localizing wires having a hook-like configuration, the localizing wire does not puncture the tissue, whereas the prior art localizing wires puncture the tissue, complicating, if not precluding, removal of the localizing wire from the tissue. Furthermore, the localizing wire described herein can be removed from the tissue without the necessity of reinserting a cannula into the tissue, thereby minimizing injury and discomfort to the patient.

It should be noted that while all of the embodiments disclose an anchor with a completely bounded area that varies in size as the anchor is reconfigured from the release to the anchor configuration, it is within the scope of the invention for the anchors not to completely bound an area. For example, the end 43 need not be attached to the thread 42. Instead, the end 43 could be unattached and be shaped to follow the leg 47 or ring 48. The end 43 could even be excluded and the leg 47 or ring 48 could just terminate prior to the thread 42. In either of these configurations, the area would be effectively bounded, not actually bounded and the bound area would be an effectively bound area. Thus, the term area as used in this application includes both an actually bound area and an effectively bound area.

Figure 11:
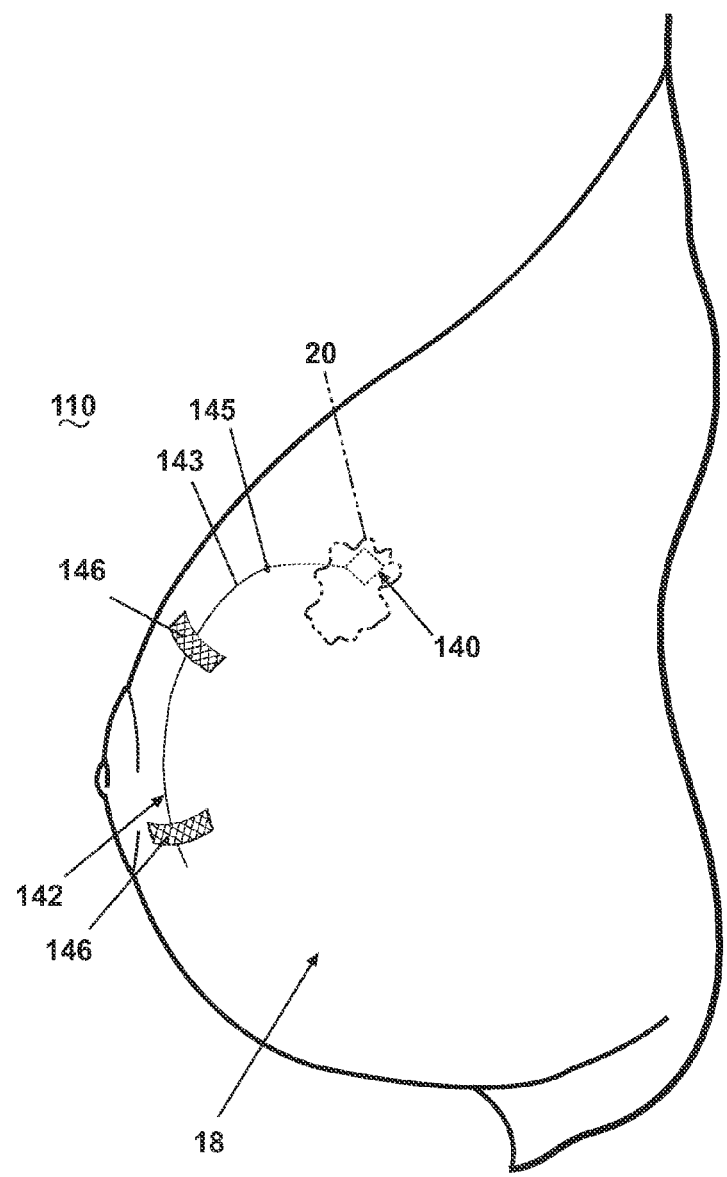
FIG. 11 is a drawing similar to FIG. 10E but using a second embodiment of the localizing wire that is configured to lay against the exterior of the tissue mass after insertion.

FIG. 11 illustrates an alternative embodiment localizing wire 110 comprising an anchor 140 and thread 142, with at least the thread 142 being configured such that the exterior portion 143 of the thread 142 will lie substantially flat against the exterior of the tissue 18. The ability of the thread 142 to lie against and not project substantially above the tissue 18 significantly reduces the likelihood that the thread 142 will be accidentally caught or hooked on a person, machine or other object. This significantly reduces the likelihood that the anchor 140 will be dislodged from the position selected by the medical professional. If the anchor 140 was moved from its initial position, it would reduce the efficacy of the wire 110 in marking the biopsy site or lesion. The ability of the thread 142 to lie substantially flat against the tissue 18 also reduces the likelihood of trauma to the tissue 18 caused by the jerking of the wire 110. Tape 146 or another similar material can be used to hold the thread 142 in place against the exterior of the tissue 18.

Two factors are believed to be most relevant to configure the localizing wire 110 such that the thread 142 lies substantially flat against the exterior of the tissue 18: the second moment of area, I, and the Young's Modulus, E, of the material. The second moment of area, I, is a physical property of the wire. It is representative of the distribution of the mass of the object relative to the objects geometric axis. The greater the mass is distributed from the geometric axis, the greater the value of 1, and the more resistant the object is to bending about the geometric axis.

The Young's Modulus essentially defines the stiffness of the material. All things being equal, the greater the Young's Modulus of a material, the greater the material will resist deflection.

In the context of a localizing wire, the Young's Modulus provides more room for adjustment to get the wire to lay flat against the tissue mass. This is because the cross-sectional area of the localizing wire has become somewhat standardized along with the cannula. Thus, the Young's Modulus is the best candidate for ensuring that the external portion of the localizing wire will lie substantially flat against the tissue.

Regardless of which factor provides the most room for adjustment, ultimately what is required is that the second moment of area and the Young's Modulus are selected such that the exterior portion of the localizing wire can be bent over and held against the tissue mass by a suitable fastener, such as tape. Preferably, the second moment of area and the Young's Modulus are selected such that the bending does not result in plastic deformation of the localizing wire as such deformation is more likely to cause the portion of the localizing wire within the tissue mass to move, which might negate the marking functionality of the localizing wire. It is more preferred that the second moment of area and the Young's Modulus are selected such that the external portion of the localizing wire bends as needed under its own weight.

While it is preferred that the bending occur immediately at or around the insertion point 145 of the localizing wire into the tissue mass, it is not necessary. If the localizing wire does not bend near the insertion point 145 before the localizing wire lies flat against the tissue, a gap will form between the localizing wire and the tissue thereby effectively creating a small loop on which something could catch. The smaller this loop, the less likely an object will catch it. Thus, this loop should be minimized, but it should be done is such a way that does not cause the shifting of the internal portion of the localizing wire, which would negate the marking functionality.

Figure 12:
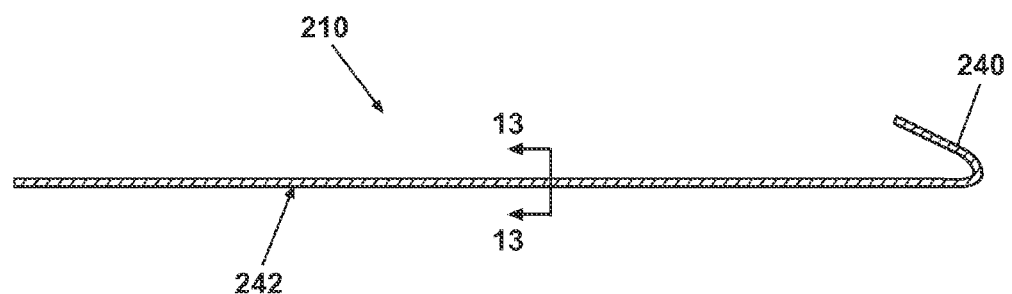
FIG. 12 is a side view of one embodiment of a localizing wire configured to lie substantially flat against the exterior of the tissue mass.
Figure 13:
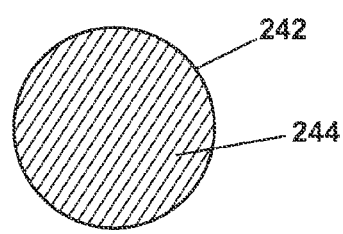
FIG. 13 is a sectional view taken along line 13-13 of FIG. 12 and illustrating the cross-sectional area of the localizing wire.

The "lying flat" functionality can be applied to any type of localizing wire and not just the localizing wires shown in FIGS. 1-10E. For example, FIGS. 12 and 13 illustrate a localizing wire 210 configured to lie flat against the exterior of the tissue mass and comprising a straight thread 242 and a hook-shaped anchor 240. The thread has a generally circular cross section 244. Other cross sections can be used, such as oval, square, polygonal, and they can be either hollow or solid.

The circular cross section 244 as illustrated is typical of current localizing wires that do not have the lie flat functionality. Thus, to achieve the lie flat functionality, the localizing wire is made from a material that provides a Young's Modulus that when combined with the cross section will permit the thread 242 to lie flat against the tissue 18. For the described cross section, a suitable material is annealed steel. The annealing of the steel reduces the stiffness of the material, which reduces the Young's Modulus, to permit the bending of the thread 242 as needed to lie flat.

It is most preferred that localizing wire 242 bends as needed to lie flat under its own weight. Thus, the portion of the thread 242 extending exteriorly of the tissue preferably has sufficient mass to effect the bending. For the example illustrated, the length of the thread preferably takes into account a suitable safety margin to ensure that there is enough thread 242 exterior of the tissue mass to effect the bending.

It is worth noting that not the entire length of the thread need be configured to effect the lying flat of the thread on the exterior of the tissue mass. This portion of the thread can be referred to as the bending portion, which may extend along all or only a portion of the thread. It is anticipated that only that portion of the thread generally near the insertion point 145 into the tissue mass need be so configured if the bending is to minimize any gap between the exterior of the tissue and the thread. However, it is anticipated that for manufacturing simplicity, the entire thread will be so configured, especially if the material is treated to select the desired Young's Modulus.

Figure 14:
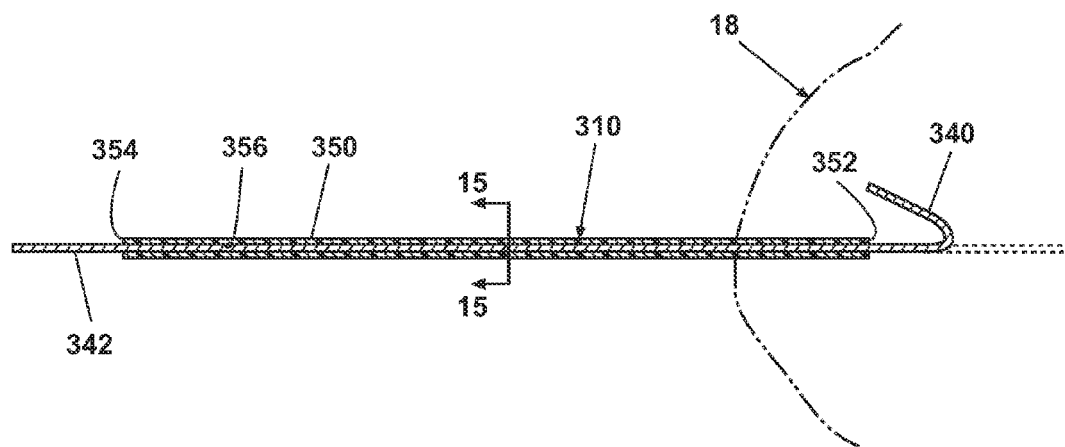
FIG. 14 is a longitudinal sectional view of another embodiment of a repositionable and removable localizing wire comprising a localizing wire with a reconfigurable anchor and an actuator in the form of a sheath for reconfiguring the anchor, with the anchor shown in an anchoring configuration and a release configuration (phantom lines).
Figure 15:
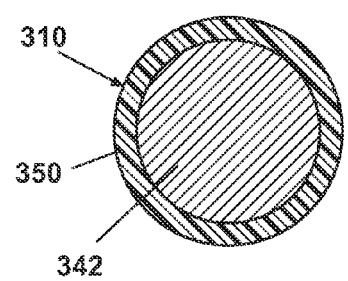
FIG. 15 is a sectional view taken along line 15-15 of FIG. 14.
Figure 16:
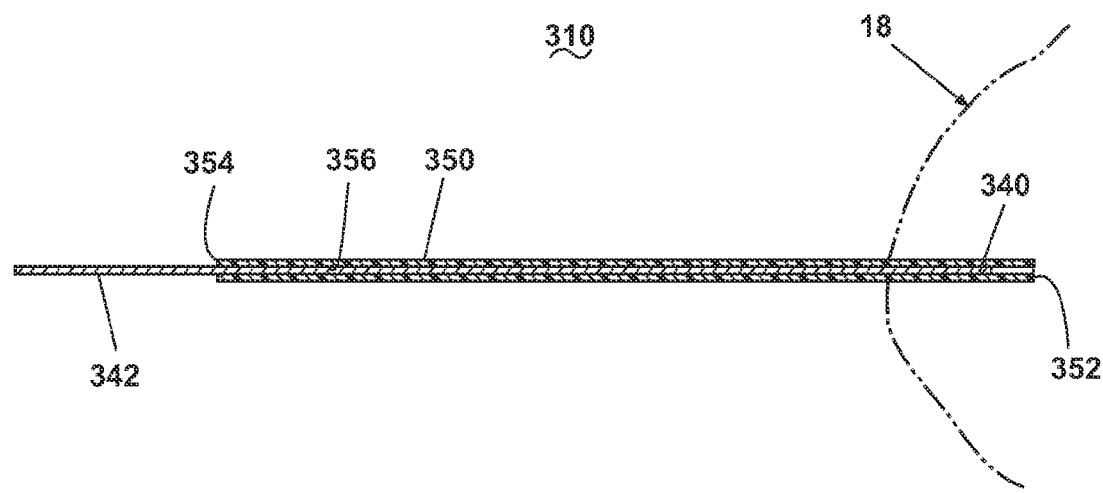
FIG. 16 is a longitudinal sectional view similar to FIG. 14, except that the sheath is moved relative to the localizing wire to effect the reconfiguring of the anchor from the anchoring configuration to the release configuration, with the anchor being retracted within the sheath.

FIGS. 14-16 illustrate another embodiment of a localizing wire 310 that can be repositioned like the localizing wire 10. Additionally, the localizing wire 310 can be withdrawn from the tissue mass 18 after the localizing wire 310 is implanted and after the removal of the cannula 14, without the reintroduction of the cannula 14.

The localizing wire 310 comprises a configurable anchor 340 and a thread 342. An actuator for reconfiguring the configurable anchor in the form of a sheath 350 is slidably mounted on the thread 342. As illustrated, the anchor 340 is made of a resilient material, such as Nitenol, that permits the anchor 340 to be configured between an anchoring configuration (FIG. 13), where it has a hook-like shape for anchoring in the tissue mass, and a release configuration (shown in phantom in FIG. 14), where the anchor is generally straight relative to the thread 342 to release the anchor 340 from the tissue mass 18.

It should be noted that while the anchor 340 illustrated in FIGS. 14-16 is known in the art, other configurable anchors, such as those shown in FIGS. 1-9, can also be used.

The sheath 350 has a proximal end 352 near the anchor 340 and an opposing distal end 354. The sheath 350 defines a hollow interior 356 in which the thread 342 is received to slidably couple the sheath 350 and thread 342 for relative slidable movement. The sheath 350 functions as an actuator for moving the anchor between the anchoring and release configurations. When the sheath 350 is withdrawn from the anchor 340 (FIG. 14), the anchor 340 because of its resiliency will inherently assume the anchoring configuration. To effect a change in the configuration of the anchor 340, the sheath 350 is advanced toward the anchor 340 by the relative movement of the thread 342 and sheath 350. As the proximal end 352 of the sheath 350 is advanced toward the anchor 340, the proximal end 352 comes into contact with the anchor 340. The continued advancement of the sheath 350 causes the anchor 340 to straighten as it is received within the interior 356 of the sheath 350 and thereby effect the reconfiguring of the anchor 340 into the release configuration.

It should be noted that the anchor 340 need not be completely received within the interior 356 of the sheath 350 for the anchor 340 to be in the release configuration. The anchor 340 need only be straightened enough that the anchor will release from the tissue. The complete receipt of the anchor 340 in the interior 356 of the sheath 350 is preferred as that ensures that the anchor 340 is straight enough and it will cause the least amount of tissue damage when the localizing wire is moved or withdrawn.

The sheath 340 is illustrated as being transparent, but it can have any desired degree of opacity. The sheath 340 is preferably made from a suitable plastic. The sheath 340 can also have any suitable type of imageable markings that permit the location of the sheath 340, especially the proximal end 352, which would permit the user to view the relative location of the proximal end 352 and the anchor 340, which can also have such imageable markings. Such imageable markings are well known in the art and vary on the type of imaging technique being used.

The implanting of the localizing wire 310 is essentially identical to that described for the localizing wire 10. In short, an introducer, typically a cannula 14, is inserted into the tissue mass 18. The localizing wire is inserted through the lumen of the cannula and out the open end of the cannula, where the anchor 340 can anchor in the tissue mass 18. Once the localizing wire is properly positioned, the cannula 14 is withdrawn.

The localizing wire 310 can be inserted along with the cannula 14 or after the cannula 14 is inserted. The localizing wire 310 can be inserted with the anchor 340 either in the anchoring configuration or the release configuration. If it is inserted in the release configuration, it will, of course, need to be put in the anchoring configuration to anchor.

After the withdrawal of the cannula 14, the localizing wire 310 can be repositioned or withdrawn without the need for reinserting the cannula 14, as is now required. The localizing wire 310 can be repositioned or withdrawn by relatively moving the thread 342 and sheath 350 such that the anchor is reconfigured from the anchoring configuration to the release configuration. In the release configuration, the localizing wire can be repositioned or withdrawn. If repositioned, the sheath 350 and thread 342 are relatively moved to configure the anchor in the anchoring configuration and re-anchor the localizing wire. If withdrawn, the user merely pulls on the exterior portion of the localizing wire 310.

The reconfiguring of the anchor 340 after the implanting of the localizing wire 310, can be done by manipulating the portions of the sheath 350 and thread 342 (sliding them relative to each other) that extend exteriorly of the tissue mass. This prevents the need for reinserting the cannula 14 as is currently done.

The ability to remove the localizing wire 310 without the reintroduction of the cannula 14 is very beneficial. Often the localizing wire 310 will be inserted in a tissue mass at the location of a biopsy site. The localizing wire 310 is left in while analysis is run on the biopsy specimen. It can take from a few hours to a few days to complete the analysis. This is too long of a time to leave the cannula 14 inserted in the patient as the rigid cannula 14 is uncomfortable, if not painful, when left in. It can also increase the risk of infection since the lumen of the cannula 14 creates an open air pathway into the tissue mass 18. In cases where the analysis confirms that no follow-up surgical procedure need be done, such as a tissue removal, the localizing wire can easily be removed without reintroducing the cannula 14, eliminating additional tissue damage and discomfort for the patient, not to mention the cost of the cannula insertion procedure.

It should be noted that the cannula 14 need not be completely withdrawn from the tissue mass for the sheath 340 to be used to effect the reconfiguring of the anchor. The cannula 14 need only be withdrawn away from the anchor a sufficient amount such that the cannula 14 does not interfere with the reconfiguring of the anchor. It is expected that in most cases the cannula will be complete removed because of the increased risk of infection and accidental tissue damage if it is left in placed, especially since the cannula will no longer be needed for the removal of the localizing wire because of the sheath.

It should also be noted that during insertion the anchor could extend beyond the end of the sheath but would still be constrained in the release configuration by the cannula, and the withdrawal of the cannula away from the anchor would effect the reconfiguration of the anchor to the anchor configuration. The sheath could then be used to reconfigure the anchor from the anchor configuration to the release configuration when it is desired to remove the localizing wire.

Figure 17:
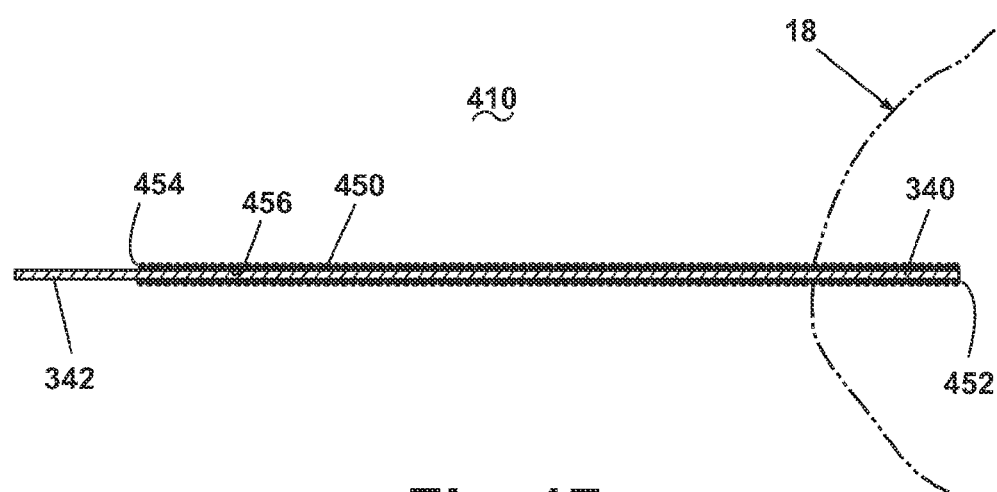
FIG. 17 is a longitudinal sectional view similar to FIG. 14 and illustrating an alternative sheath in the form of a coil spring.

FIG. 17 illustrates an alternative localizing wire 410 having an alternative design for the sheath in the form of a coil spring 450. The coil spring 450 is wound such that it defines a hollow interior 456 for receiving the thread 342. The coil spring 450 has a proximal end 452 and a distal end 454. The operation of the localizing wire 410 with the coil spring 450 is identical to that previously described.

The localizing wires 310 and 410 can be configured to lay flat against the exterior of the tissue mass 18 as previously described. With the localizing wires 310, 410, the characteristics of both the thread 342, 442 and the sheath 350, 450 must be taken into account to achieve the laying flat functionality.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

What is claimed is:

1. A method of marking a lesion in a tissue mass in a patient, the method comprising:
   providing a localizing wire and a tube having at least one lumen, the localizing wire comprising a localizing thread and a localizing anchor having a collapsed shape delineating a first bounded area when the localizing anchor is in the at least one lumen and an expanded shape delineating a second bounded area when the localizing anchor is outside the at least one lumen, wherein the second bounded area results from an area expansion of the first bounded area;
   inserting the tube, with the localizing anchor in the collapsed shape in the at least one lumen, into the tissue mass;
   moving one of the localizing wire and the tube to place the localizing anchor outside the at least one lumen at a first selected location relative to the lesion to release the anchor from the collapsed shape to expand to the expanded shape for exerting an expansive force by the localizing anchor against the tissue mass without puncturing the tissue mass at the first selected location relative to the lesion,
   wherein the collapsed shape is defined by four angled internal corners with only one internal corner being greater than 90 degrees, and the expanded shape is a triangle.

2. The method according to claim 1, and retracting the localizing anchor into the at least one lumen to return the localizing anchor from the expanded shape to the collapsed shape.

3. The method according to claim 2, and repositioning the tube to relocate the localizing member at a second selected location relative to the lesion.

4. The method according to claim 1, and withdrawing the tube from the tissue mass with the localizing anchor remaining in the first selected location and the localizing thread extending exterior of the tissue mass.

5. The method according to claim 4, and reinserting the tube into the tissue mass with the localizing thread extending through the at least one lumen.

6. The method according to claim 5, and retracting the localizing anchor into the at least one lumen to return the localizing anchor from the expanded shape to the collapsed shape.

7. The method according to claim 6, and withdrawing the tube with the localizing wire therein to remove the localizing wire from the tissue mass.

8. The method according to claim 1, wherein providing a tube comprises providing one of a cannula and a sheath.

9. A method of marking a lesion in a tissue mass in a patient, the method comprising:
   providing a localizing wire and a tube having at least one lumen, the localizing wire comprising a localizing thread and a localizing anchor having a collapsed shape delineating a first bounded area when the localizing anchor is in the at least one lumen and an expanded shape delineating a second bounded area when the localizing anchor is outside the at least one lumen, wherein the second bounded area results from an area expansion of the first bounded area;
   inserting the tube, with the localizing anchor in the collapsed shape in the at least one lumen, into the tissue mass; and
   moving one of the localizing wire and the tube to place the localizing anchor outside the at least one lumen at a first selected location relative to the lesion to release the anchor from the collapsed shape to expand to the expanded shape for exerting an expansive force by the localizing anchor against the tissue mass without puncturing the tissue mass at the first selected location relative to the lesion,
   wherein the collapsed shape is substantially a figure eight shape and the expanded shape is a circle.

10. The method according to claim 9, and retracting the localizing anchor into the at least one lumen to return the localizing anchor from the expanded shape to the collapsed shape.

11. The method according to claim 10, and repositioning the tube to relocate the localizing member at a second selected location relative to the lesion.

12. The method according to claim 9, and withdrawing the tube from the tissue mass with the localizing anchor remaining in the first selected location and the localizing thread extending exterior of the tissue mass.

13. The method according to claim 12, and reinserting the tube into the tissue mass with the localizing thread extending through the at least one lumen.

14. The method according to claim 13, and retracting the localizing anchor into the at least one lumen to return the localizing anchor from the expanded shape to the collapsed shape.

15. The method according to claim 14, and withdrawing the tube with the localizing wire therein to remove the localizing wire from the tissue mass.

16. The method according to claim 9, wherein providing a tube comprises providing one of a cannula and a sheath.

17. A method of marking a lesion in a tissue mass in a patient, the method comprising:
   providing a localizing wire and a tube having at least one lumen, the localizing wire comprising a localizing thread and a localizing anchor having a collapsed shape delineating a first bounded area when the localizing anchor is in the at least one lumen and an expanded shape delineating a second bounded area when the localizing anchor is outside the at least one lumen, wherein the second bounded area results from an area expansion of the first bounded area;

inserting the tube, with the localizing anchor in the collapsed shape in the at least one lumen, into the tissue mass;

moving one of the localizing wire and the tube to place the localizing anchor outside the at least one lumen at a first selected location relative to the lesion to release the anchor from the collapsed shape to expand to the expanded shape for exerting an expansive force by the localizing anchor against the tissue mass without puncturing the tissue mass at the first selected location relative to the lesion, wherein each of the collapsed shape and the expanded shape is a four sided polygon.

18. The method according to claim 17, and retracting the localizing anchor into the at least one lumen to return the localizing anchor from the expanded shape to the collapsed shape.

19. The method according to claim 18, and repositioning the tube to relocate the localizing member at a second selected location relative to the lesion.

20. The method according to claim 17, comprising:

withdrawing the tube from the tissue mass with the localizing anchor remaining in the first selected location and the localizing thread extending exterior of the tissue mass;

reinserting the tube into the tissue mass with the localizing thread extending through the at least one lumen;

retracting the localizing anchor into the at least one lumen to return the localizing anchor from the expanded shape to the collapsed shape; and withdrawing the tube with the localizing wire therein to remove the localizing wire from the tissue mass.

* * * * *